United States Patent [19]

Liang et al.

[11] Patent Number: 5,502,257
[45] Date of Patent: Mar. 26, 1996

[54] PROCESS FOR THE PRODUCTION OF CYCLOPROPANECARBOXALDEHYDE

[75] Inventors: Shaowo Liang, Kingsport; Timothy W. Price, Church Hill; Timothy R. Nolen; Daniel B. Compton, both of Kingsport; David C. Attride, Gray, all of Tenn.

[73] Assignee: Eastman Chemical Company, Kingsport, Tenn.

[21] Appl. No.: 391,793

[22] Filed: Feb. 21, 1995

[51] Int. Cl.$^6$ .......................... C07C 47/293; C07C 47/28
[52] U.S. Cl. .......................... 568/433; 568/427; 568/450
[58] Field of Search .................................. 568/443, 450

[56] References Cited

U.S. PATENT DOCUMENTS

| | | | |
|---|---|---|---|
| 3,932,468 | 1/1976 | Kurkov | 260/347.1 |
| 4,275,238 | 6/1981 | Petree et al. | 564/446 |
| 4,897,498 | 1/1990 | Monnier et al. | 549/534 |

*Primary Examiner*—Werren B. Lone
*Attorney, Agent, or Firm*—J. Frederick Thomsen; Harry J. Gwinnell

[57] ABSTRACT

Disclosed is a process for the preparation of cyclopropanecarboxaldehyde by the thermal isomerization of 2,3-dihydrofuran under superatmospheric pressure, e.g., at a temperature of about 300° to 600° C. and a pressure of about 3 to 345 bars absolute.

5 Claims, No Drawings

PROCESS FOR THE PRODUCTION OF CYCLOPROPANECARBOXALDEHYDE

This invention pertains to a process for the preparation of cyclopropanecarboxaldehyde from 2,3-dihydrofuran. More specifically, this invention pertains to the preparation of cyclopropanecarboxaldehyde by heating 2,3-dihydrofuran under superatmospheric pressure.

Cyclopropanecarboxaldehyde and derivatives are important synthetic building blocks for introducing the cyclopropane group into chemical compounds useful as human and veterinary drugs and pesticides. See, for example, European Patent Publications EP 237,955 A2, EP 273,862 A2, EP 408,034 and EP 430,847 A1, Published PCT Application WO 91/09849, and U.S. Pat. No. 4,275,238.

The derivation of 2,3-dihydrofuran (2,3-DHF) from butadiene is described in U.S. Pat. No. 5,254,701. The overall scheme comprises the monoepoxidation of butadiene to produce 3,4-epoxy-1-butene which is rearranged to 2,5-dihydrofuran which then is rearranged to 2,3-DHF. 2,5-Dihydrofuran undergoes isomerization to 2,3-DHF in 96.1% yield via $RuClH(CO)(Ph_3P)_3$ catalysis at 65° C. in 2.5 hours. The initial steps, epoxidation and isomerization to 2,5-dihydrofuran, are described in U.S. Pat. Nos. 4,897,498 and 3,932,468.

The thermal isomerization or rearrangement of 2,3-DHF to cyclopropanecarboxaldehyde (CPCA) at atmospheric pressure has been described by C. L. Wilson, *J. Amer. Chem. Soc.*, 69, pp. 3002–3004 (1947)]. The isomerization reported by Wilson consisted of passing 2,3-DHF through a packed column heated at 375°–540° C. Excessive residence times were used, resulting in low selectivities of CPCA, e.g., 10 to 40%, versus other products. The major byproducts were crotonaldehyde, carbon monoxide and propylene. The space-time yield was less than 25 g CPCA per liter-hour wherein the space-time yield is the grams of CPCA produced per liter of heated reactor space per hour.

U.S. Pat. No. 4,275,238 describes a similar process using an open reactor instead of a packed column. The isomerization of 2,3-DHF takes place at 460°–480° C. and at atmospheric pressure. The conversion of 2,3-DHF on each pass was only in the range of 2–9%. The selectivity of the formation of CPCA versus crotonaldehyde was about 93%. Again, since the process is carried out under atmospheric pressure, the space-time yields are very low, i.e., only in the range of 30 to 80 g CCPA/L-hour. Prolonged heating results in the formation of byproduct crotonaldehyde which occurs via further isomerization of the product cyclopropanecarboxaldehyde.

We have discovered that the rate of reaction of 2,3-DHF to CPCA is substantially higher at super-atmospheric pressures as compared to reaction rates at atmospheric pressure. Thus, the present invention provides a process for the preparation of CPCA which comprises heating 2,3-DHF at a temperature of about 300° to 600° C. and a pressure of about 3 to 345 bars absolute. We have found that higher pressures result in increased reaction rates, while selectivity is not affected. The present process therefore provides a means for the synthesis of CPCA at higher production rates per unit reactor volume (referred to herein as space-time yield defined as the grams of CPCA produced per liter of heated reactor space per hour). Another advantage of the process of this invention is that the use of higher reaction pressures permits one to achieve a desired space-time yield and selectivity at lower reaction temperatures. Such lower reaction temperatures reduce the fouling in the reactor and require less heat input per unit of reactor feed.

Although the novel isomerization process is believed to be operable over pressures of from about 3 to 345 bars absolute, pressures in the range of about 4.5 to 35.5 bars absolute are preferred with a range of 4.5 to 15 bars absolute being most preferred. It is also preferred to operate the process at temperatures in the range of about 350° to 550° C.

The process of this invention may be carried out in a batch, semi-continuous or continuous mode of operation. The process preferably is operated in a continuous mode using a gas phase reaction system wherein 2,3-DHF vapor is fed continuously to, and isomerization product comprising CPCA is continuously removed from, a heated reactor unit. The isomerization product removed from may be fed continuously to a distillation unit wherein the crude product is distilled to recover the unreacted 2,3-DHF as the overhead product and CPCA is taken (underflowed) from the bottom or base of the distillation column. The recovered 2,3-DHF may be returned to the reactor feed tank or used to manufacture other chemicals.

The purity of the 2,3-DHF used in the present invention is not an important factor in the conversion of 2,3-DHF to CPCA. For example, 2,3-DHF containing other components such as furan, tetrahydrofuran, 2,5-dihydrofuran or a mixture thereof in total amounts of up to 40 weight percent of the total weight of the 2,3-DHF feed material gives satisfactory results in terms of conversions and selectivities. The process also may be carried out using a gaseous 2,3-DHF feed which contains up to 95 volume percent of an inert gas such as nitrogen, hydrogen, helium, argon or carbon dioxide. Although the use of an inert gas is not essential, practical considerations such as the need to control reactor pressure may be facilitated by the use of an inert gas.

The rate of feed of 2,3-DHF in continuous, gas phase operation can be varied widely depending upon other process parameters such as the temperatures and pressures used and the degree of conversion desired. Gas hourly space velocities (GHSV—the unit volume of 2,3-DHF fed per unit volume of heated reactor space per hour) in the range of about 100 to 4600 may be used although GHSV values in the range of about 300 to 2500 are more typical.

A preferred embodiment of the present invention is the preparation of CPCA which comprises the steps of:

(1) feeding a gaseous mixture comprising 2,3-DHF and an inert diluent in a 2,3-DHF:inert diluent volume ratio of about 1:0.01 to 1:10 to a reaction zone maintained at a temperature of about 300° to 600° C. and a pressure of about 4.5 to 35.5 bars absolute; and (2) removing a gaseous isomerization product comprising CPCA from the reaction zone.

The novel process provided by the present invention is further illustrated by the following examples. The examples utilized a gas phase reaction unit consisting of a feed tank, a preheating line, a reactor constructed of stainless steel tubing 30 cm in length having an inside diameter of 2.5 cm and packed with quartz chips, a condenser and a receiver. The reactor had a volume of 0.15 liter and was heated with an electric furnace. The pressure within the reactor was regulated by means of a back pressure regulator. Nitrogen was metered into the preheating line at a rate of 100 mL per minute. An even flow of 2,3-DHF having a purity of 99% was pumped from the feed tank into the preheating line wherein the mixture of 2,3-DHF and nitrogen was heated at 310° C. and fed to the reactor. Temperatures within the reactor space were monitored by a thermowell containing two thermocouples which were placed 7.6 cm and 27 cm from the entrance to the heated section of the tube. The temperatures reported in the examples are averages of the two temperatures.

The isomerization product removed from the reactor was cooled by passing it through the condenser and collected in the receiver. This mixture was fed continuously to the middle of a distillation column. The base of the column was heated at 100° to 102° C. CPCA was recovered from the base of the column and unreacted 2,3-DHF was collected in a distillate receiver and continuously recycled to the feed tank.

The conversions and selectivities reported in the example were determined by gas chromatographic (GC) analyses performed on a Hewlett-Packard 5890 series II gas chromatography with a 30 meter DB-Wax and a 30 meter DB-17 capillary columns. The identities of the products obtained were confirmed by nuclear magnetic resonance spectrometry and gas chromatography-mass spectrometry comparing the spectra to those of authentic samples purchased from Aldrich Chemical.

EXAMPLES 1–8

2,3-DHF was isomerized according to the procedure described above using different temperatures, a pressure of 5.8 bar absolute and a 2,3-DHF feed rate of 13 g 2,3-DHF per minute. The experiments constituting Examples 1–8 were carried out for a sufficient length of time to attain steady-state conditions. The results obtained in these examples are set forth in Table I wherein "Temp" is the average temperature described above in °C. at which the experiment was carried out, "STY" is the space-time yield defined as the grams of CPCA produced per liter of heated reactor space per hour, "2,3-DHF Conv" is the mole percent conversion of 2,3-DHF defined as:

Moles 2,3-DHF converted to products/Moles 2,3-DHF fed×100 and "CPCA Select" is the mole percent selectivity to CPCA defined as:

Moles 2,3-DHF converted to CPCA/(Moles 2,3-DHF converted to CPCA+HCr)×100 wherein HCr is crotonaldehyde.

TABLE I

| Example | Temp | 2,3-DHF Conv | CPCA Select | STY |
|---|---|---|---|---|
| 1 | 376 | 2 | 95 | 121 |
| 2 | 392 | 3 | 95 | 163 |
| 3 | 399 | 3 | 95 | 161 |
| 4 | 406 | 6 | 95 | 264 |
| 5 | 413 | 8 | 94 | 381 |
| 6 | 419 | 11 | 93 | 522 |
| 7 | 426 | 16 | 93 | 759 |
| 8 | 432 | 22 | 92 | 1025 |

EXAMPLES 9–16

The procedure described above for Examples 1–8 is repeated for the isomerization of 2,3-DHF to CPCA at different temperatures using a pressure of 4.5 bar absolute and a 2,3-DHF feed rate of 10.2 g per minute. The results obtained in Examples 9–16 are set forth in Table II wherein "Temp", "STY", "2,3-DHF Conv" and "CPCA Select" have the meanings given above.

TABLE II

| Example | Temp | 2,3-DHF Conv | CPCA Select | STY |
|---|---|---|---|---|
| 9 | 380 | 2 | 100 | 68 |
| 10 | 391 | 2 | 97 | 94 |
| 11 | 400 | 3 | 96 | 135 |
| 12 | 406 | 6 | 96 | 215 |
| 13 | 413 | 8 | 95 | 322 |
| 14 | 419 | 12 | 94 | 450 |
| 15 | 426 | 17 | 93 | 636 |
| 16 | 433 | 23 | 92 | 817 |

EXAMPLES 17–23

The procedure described above for Examples 1–8 is repeated for the isomerization of 2,3-DHF to CPCA at different temperatures using a pressure of 3.1 bar absolute and a 2,3-DHF feed rate of 6.5 g per minute. The results obtained in Examples 17–23 are set forth in Table III wherein "Temp", "STY", "2,3-DHF Conv" and "CPCA Select" have the meanings given above.

TABLE III

| Example | Temp | 2,3-DHF Conv | CPCA Select | STY |
|---|---|---|---|---|
| 17 | 383 | 3 | 96 | 26 |
| 18 | 393 | 5 | 96 | 121 |
| 19 | 404 | 9 | 95 | 216 |
| 20 | 419 | 12 | 94 | 276 |
| 21 | 426 | 16 | 93 | 378 |
| 22 | 433 | 22 | 92 | 510 |
| 23 | 441 | 30 | 90 | 668 |

COMPARATIVE EXAMPLES C-1–C-8

The procedure described above for Examples 1–8 is repeated for the isomerization of 2,3-DHF to CPCA at different temperatures and atmospheric pressure using a 2,3-DHF feed rate of 1.9 g per minute. The results obtained in Comparative Examples 1–8 are set forth in Table IV wherein "Temp", "STY", "2,3-DHF Conv" and "CPCA Select" have the meanings given above.

TABLE IV

| Comparative Example | Temp | 2,3-DHF Conv | CPCA Select | STY |
|---|---|---|---|---|
| C-1 | 397 | 2 | 100 | 13 |
| C-2 | 406 | 3 | 97 | 21 |
| C-3 | 414 | 4 | 95 | 26 |
| C-4 | 422 | 5 | 95 | 38 |
| C-5 | 431 | 7 | 95 | 53 |
| C-6 | 438 | 11 | 94 | 75 |
| C-7 | 446 | 16 | 93 | 106 |
| C-8 | 453 | 22 | 92 | 146 |

COMPARATIVE EXAMPLES C-9–C-16

The procedure described above for Examples 1–8 is repeated for the isomerization of 2,3-DHF to CPCA at different temperatures and atmospheric pressure using a 2,3-DHF feed rate of 6.5 g per minute. The results obtained in Comparative Examples 9–16 are set forth in Table V wherein "Temp", "STY", "2,3-DHF Conv" and "CPCA Select" have the meanings given above.

TABLE V

| Comparative Example | Temp | 2,3-DHF Conv | CPCA Select | STY |
| --- | --- | --- | --- | --- |
| C-9 | 389 | 0.8 | 100 | 16 |
| C-10 | 402 | 1.2 | 100 | 27 |
| C-11 | 412 | 1.8 | 94 | 43 |
| C-12 | 418 | 2.7 | 94 | 66 |
| C-13 | 427 | 4.1 | 95 | 100 |
| C-14 | 434 | 6.0 | 94 | 147 |
| C-15 | 440 | 8.8 | 93 | 210 |
| C-16 | 446 | 11.6 | 93 | 274 |

COMPARATIVE EXAMPLES C-17–C-24

The procedure described above for Examples 1–8 is repeated for the isomerization of 2,3-DHF to CPCA at different temperatures and atmospheric pressure using a 2,3-DHF feed rate of 10.2 g per minute. The results obtained in Comparative Examples 17–24 are set forth in Table VI wherein "Temp", "STY", "2,3-DHF Conv" and "CPCA Select" have the meanings given above.

TABLE VI

| Comparative Example | Temp | 2,3-DHF Conv | CPCA Select | STY |
| --- | --- | --- | --- | --- |
| C-17 | 384 | 0.5 | 100 | 12 |
| C-18 | 395 | 0.7 | 100 | 20 |
| C-19 | 405 | 1.0 | 100 | 33 |
| C-20 | 412 | 1.5 | 94 | 51 |
| C-21 | 420 | 2.1 | 94 | 76 |
| C-22 | 427 | 3.2 | 94 | 117 |
| C-23 | 435 | 4.8 | 94 | 182 |
| C-24 | 442 | 6.8 | 94 | 260 |

COMPARATIVE EXAMPLES C-25–C-29

The procedure described above for Examples 1–8 is repeated for the isomerization of 2,3-DHF to CPCA at different temperatures and atmospheric pressure using a 2,3-DHF feed rate of 13 g per minute. The results obtained in Comparative Examples 25–29 are set forth in Table VII wherein "Temp", "STY", "2,3-DHF Conv" and "CPCA Select" have the meanings given above.

TABLE VII

| Comparative Example | Temp | 2,3-DHF Conv | CPCA Select | STY |
| --- | --- | --- | --- | --- |
| C-25 | 376 | 0.3 | 100 | 9 |
| C-26 | 396 | 0.7 | 100 | 23 |
| C-27 | 414 | 1.5 | 94 | 65 |
| C-28 | 421 | 2.3 | 94 | 105 |
| C-29 | 429 | 3.2 | 94 | 149 |

EXAMPLE 24

The procedure described above for Examples 1–8 is repeated for the isomerization of 2,3-DHF to CPCA using a temperature of 425° C., a pressure of 11.6 bar absolute and a 2,3-DHF feed rate of 89 g per minute (GHSV=2500). CPCA is obtained in a space-time yield of 962 g/L-hour with a selectivity of 98 mole percent. Distillation provides CPCA virtually free of crotonaldehyde in a 90 mole percent yield based on the 2,3-DHF converted.

EXAMPLE 25

The procedure described above for Examples 1–8 is repeated for the isomerization of 2,3-DHF to CPCA using a temperature of 431° C., a pressure of 4.6 bar absolute and a feed rate of 10 g per minute of a mixture consisting of 73 weight percent 2,3-DHF, 13 weight percent furan, 12 weight percent tetrahydrofuran and 2 weight percent 2,5-dihydrofuran. This corresponds to a 2,3-DHF feedrate of 7.4 g per minute and a 2,3-DHF GHSV of 530. CPCA is obtained in a space-time yield of 433 g/L-hour in a selectivity of 93 mole percent.

EXAMPLE 26

This experiment was carried out using an integrated pilot plant consisting of a feed tank, preheating line, a heated reactor, condenser, product tank, distillation column, and distillate receiver. The reactor consisted of a pipe 76 cm in length having an inside diameter of 2 cm constructed of Hastelloy alloy and packed with quartz chips. A 6-point thermowell provided temperature measurements at 15 cm intervals along the reactor's central axis of symmetry. The reactor had a heated volume of 0.24 liter and was electrically heated with a 3-zone, Lindbergh furnace. Pressure was controlled at 4.5 bar absolute with a Research control valve. Nitrogen was fed to the pre-heater to provide a non-condensable component in the reactor effluent stream to aid in maintaining constant pressure. 2,3-DHF having a purity of 98% was fed continuously to the reactor at a rate of 1000 g per hour (GHSV=2000) with a nitrogen flow rate of 500 mL per minute. The reactor was maintained at an average temperature of 477° C.

The crude isomerization product removed from the reactor was passed through a condenser and the condensed product was collected in the product tank. The crude product was fed continuously to the middle of a distillation column, having a diameter of 10.2 cm and constructed of Hastelloy alloy, packed with Goodloe packing material. The base of the column was maintained at 100° to 102° C. with pressurized steam. CPCA product was recovered from the base of the column and unreacted 2,3-DHF was collected in a distillate receiver and continuously recycled to the feed tank. The 2,3-DHF recycled was essentially free of CPCA. CPCA was produced at a space-time yield of 660 g/L-hour in a selectivity of 93 mole percent.

The invention has been described in detail with particular reference to preferred embodiments thereof, but it will be understood that variations and modifications can be effected within the spirit and scope of the invention.

We claim:

1. Process for the preparation of cyclopropanecarboxaldehyde which comprises heating 2,3-dihydrofuran at a temperature of about 300° to 600° C. and a pressure of about 3 to 345 bars absolute.

2. Process according to claim 1 wherein the temperature is in the range of about 350° to 550° C. and the pressure is in the range of about 4.5 to 35.5 bars absolute.

3. Process for the preparation of cyclopropanecarboxaldehyde which comprises the steps of:

(1) feeding a gaseous mixture comprising 2,3-dihydrofuran and an inert diluent in a 2,3-dihydrofuran:inert diluent volume ratio of about 1:0.01 to 1:10 to a reaction zone maintained at a temperature of about 300° to 600° C. and a pressure of about 4.5 to 35.5 bars absolute; and (2) removing a gaseous isomerization product comprising cyclopropanecarboxaldehyde from the reaction zone.

4. Process according to claim 3 wherein the gas hourly space velocity of the 2,3-dihydrofuran feed is in the range of about 300 to 2500.

5. Process for the preparation of cyclopropanecarboxaldehyde which comprises the steps of:

(1) feeding a gaseous mixture comprising 2,3-dihydrofuran and an inert diluent in a 2,3-dihydrofuran:inert diluent volume ratio of about 1:0.01 to 1:10 to a reaction zone maintained at a temperature of about 300° to 600° C. and a pressure of about 4.5 to 35.5 bars absolute at a 2,3-dihydrofuran gas hourly space velocity of 300 to 2500; and (2) removing a gaseous isomerization product comprising cyclopropanecarboxaldehyde from the reaction zone.

* * * * *